United States Patent [19]
Fahnenstich et al.

[11] 4,093,740
[45] June 6, 1978

[54] FODDER FOR RUMINANTS

[75] Inventors: Rudolf Fahnenstich, Strotzbach; Joachim Heese, Grossauheim, both of Germany; Dyfed Lewis, Loughborough, England

[73] Assignee: Deutsche Gold- und Silber-Scheideanstalt vormals Roessier, Frankfurt, Germany

[21] Appl. No.: 330,110

[22] Filed: Feb. 16, 1973

[51] Int. Cl.$^2$ .......................................... A61K 31/195
[52] U.S. Cl. .................................................. 424/319
[58] Field of Search .......................................... 424/319

[56] References Cited

U.S. PATENT DOCUMENTS

| | | |
|---|---|---|
| 2,847,451 | 8/1958 | Schott et al. .................. 424/204 X |
| 2,879,162 | 3/1959 | Baldini et al. .................. 424/311 X |
| 2,927,859 | 3/1960 | Gordon ................................ 99/4 |
| 3,256,095 | 6/1966 | Crosby et al. .................... 424/319 |
| 3,624,114 | 11/1971 | Morelle ............................. 424/319 |
| 3,627,892 | 12/1971 | Moor ................................. 424/251 |

OTHER PUBLICATIONS

*Chemical abstracts,* vol. 67, 98167r; vol. 74, 108888, 1221382; vol. 75, 34273e, 106868c.

*Primary Examiner*—Frederick E. Waddell
*Attorney, Agent, or Firm*—Cushman, Darby & Cushman

[57] ABSTRACT

N-acyl-methionine is added to ruminant fodder.

4 Claims, No Drawings

FODDER FOR RUMINANTS

The invention is directed to the use of N-acylmethionine in fodder for ruminants, e.g. cattle, sheep, goats, deer or antelope.

It is known to add aminoacids to provender. Thus, for example, methionine effects a considerable qualitative improvement in the protein component of fodder in which this aminoacid is not present in sufficient amount for the animal, i.e. in which the protein component is poor in methionine. In this case the addition of methionine causes a considerable improvement in the growth rate and in the value of the fodder. This result, however, until now has only been produced with monogastric animals.

The feeding or nutrient physiology of ruminants differs substantially from that of monogastric animals. It is known that ruminants have several stomachs. The first, by far the greatest stomach, the paunch, contains a specific microflora of bacteria and protozoa which breakdown added synthetic aminoacids before they are utilizable for the animal (J. Animal Sc. Vol. 14(1955) pages 132–136). Besides there are found in the paunch enzyme systems which can synthesize aminoacids from ammonia and fatty acids or carbon compounds. As appears from experiments it is actually possible to nourish ruminants without any nutriment protein if there is fed sufficient nonprotein nitrogen, for example, urea and carbon compounds (see, for example, annal Sci. Fennicae A II 141 (1968), pages 3–21). For these reasons it is not expected that a qualitative improvement of the fodder of ruminants would occur by addition of aminoacids. This has been confirmed by experiments (J. Animal Sci. Vol. 9(1950) 661; Vol. 10(1951) 439–446 and 1052; Vol. 14(1955) 132–136).

It has now been found that N-acylmethionines of the formula:

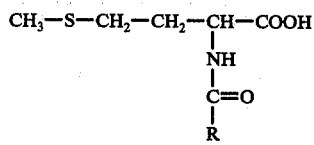

in which R is a saturated or unsaturated, straight or branched chain hydrocarbon radical, are suitable for use for fodder. Surprisingly the addition of this kind of compound as a fodder additive results in a considerable improvement, for example, in the growth of wool in sheep. Preferred are N-acyl-methionines that have 7 to 21 carbon atoms in the carbon radical. Examples of the preferred additives are N-stearoyl-methionine, N-oleoylmethionine, N-decanoyl-methionine, N-isodecanoyl methionine, N-pelargonoyl-methionine, N-lauroyl-methionine, N-palmitoyl-methionine, N-arachidoyl-methionine, N-behenoyl-methionine, N-delta-9-decylenoyl-methionine, N-palmitoleoyl-methionine, N-linoleoyl-methionine, N-myristoyl-methionine, N-eleostearoyl-methionine, N-cetoleoyl-methionine, N-octenoyl-methionine and N-capryloyl-methionine. Other but less preferred N-acyl compounds are N-acetyl-methionine, N-pivaloyl-methionine, N-acryloyl-methionine, N-propionyl methionine, N-caproyl-methionine, N-butyryl-methionine, N-valeroyl-methionine and N-isovaleroyl-methionine.

In addition to sheep, as stated, the N-acyl-methionine can be added to the fodder of other ruminants such as cattle, goats, deer and antelope, for example.

The N-acyl-methionine compounds used in the invention can be made by known methods, for example, by reaction of methionine with the corresponding acid chloride, e.g. stearoyl chloride, oleoyl chloride, decanoyl chloride, capryloyl chloride, caproyl chloride or acetyl chloride in the presence of alkali, e.g. sodium hydroxide or potassium hydroxide.

The N-acyl-methionines can be added directly to fodder. Generally they are admixed with customary fodders or provender or they can be used with premixtures such as vitamin and mineral mixtures or they can be used with urea-fodder.

The amount of N-acyl-methionine employed can vary within wide ranges. Usually based on the entire amount of fodder for one day the amount of N-acyl-methionine being such as to provide methionine is about 0.01 to 5% based on the dry material of the fodder, preferably about 0.03 to 1%.

Unless otherwise indicated, all parts and percentages are by weight.

EXAMPLE 1

The experimental animals were 12 male sheep (Merinos). As the base fodder there was used for each animal daily 1000 to 1300 grams of a mixture of 10.8% grass meal, 44.9% oat shell meal, 42.9% tapioca, 0.86% urea and 0.54% mineral mixture for cattle. In a preliminary period of 5 weeks all of the animals were supplied exclusively with this base fodder. In a subsequent main period of 5 weeks they were fed in three different groups containing 4 animals each:

Group I animals 1 to 4, only base fodder.

Group II animals 5 to 8, daily addition of 5.0 grams of methionine to the base fodder.

Group III animals 9 to 12, daily addition of 13.9 grams of N-stearoyl-methionine to the base fodder.

At the end of the preliminary and the main periods the yield of wool on each animal was determined from areas defined by tattoing. The results are set forth in the following table:

|  |  | Preliminary Period Wool Yield | | Main Period Wool Yield | |
| --- | --- | --- | --- | --- | --- |
|  |  | Grams | % of Group I | Grams | % of Group I |
| Group I | animal 1 | 77.4 |  | 73.9 |  |
|  | animal 2 | 58.2 |  | 53.9 |  |
|  | animal 3 | 65.2 |  | 59.9 |  |
|  | animal 4 | 64.4 |  | 66.7 |  |
| Group Average |  | 65.5 | 100 | 63.6 | 100 |
| Group II | animal 5 | 61.5 |  | 63.1 |  |
|  | animal 6 | 68.9 |  | 65.6 |  |
|  | animal 7 | 58.2 |  | 57.9 |  |
|  | animal 8 | 76.3 |  | 79.3 |  |
| Group Average |  | 66.2 | 101 | 66.5 | 104 |
| Group III | animal 9 | 58.2 | % of Gr. I | 71.1 | % of Gr. I |
|  | animal 10 | 64.3 |  | 80.8 |  |
|  | animal 11 | 73.2 |  | 87.1 |  |
|  | animal 12 | 65.4 |  | 86.7 |  |
| Group Average |  | 64.2 | 98 | 81.3 | 128 |

EXAMPLE 2

The process was the same as in example 1 except that in the main period the 4 animals in Group III were given daily 13.9 grams of N-oleoyl-methionine instead of N-stearoyl-methionine as the base fodder additive.

|  |  | Preliminary period Wool Yield | | Main Period Wool Yield | |
| --- | --- | --- | --- | --- | --- |
|  |  | Grams | % of Group I | Grams | % of Group I |
| Group I | animal 1 | 74.4 |  | 73.9 |  |
|  | animal 2 | 58.2 |  | 53.9 |  |
|  | animal 3 | 65.2 |  | 59.9 |  |
|  | animal 4 | 64.4 |  | 66.7 |  |
| Group Average |  | ;65.5 | 100 | 63.6 | 100 |
| Group II | animal 5 | 61.5 |  | 63.1 |  |
|  | animal 6 | 68.9 |  | 65.6 |  |
|  | animal 7 | 58.2 |  | 57.9 |  |
|  | animal 8 | 76.3 |  | 79.3 |  |
| Group Average |  | 66.2 | 101 | 66.5 | 104 |
|  |  |  | % of Gr. I |  | % of Gr. I |
| Group III | animal 13 | 62.9 |  | 80.5 |  |
|  | animal 14 | 65.1 |  | 79.3 |  |
|  | animal 15 | 73.6 |  | 87.4 |  |
|  | animal 16 | 57.4 |  | 78.7 |  |
| Group Average |  | 64.8 | 99 | 83.1 | 138 |

EXAMPLE 3

The process was the same as in example 1 except that in the main period the 4 aminals in Group III were given daily 10.2 grams of N-decanoyl-methionine instead of N-stearoyl-methionine as the fodder additive.

|  |  | Preliminary Period Wool Yield | | Main Period Wool Yield | |
| --- | --- | --- | --- | --- | --- |
|  |  | Grams | % of Group I | Grams | % of Group I |
| Group I | animal 1 | 74.4 |  | 73.9 |  |
|  | animal 2 | 58.2 |  | 53.9 |  |
|  | animal 3 | 65.2 |  | 59.9 |  |
|  | animal 4 | 64.4 |  | 66.7 |  |
| Group Average |  | 65.5 | 100 | 63.6 | 100 |
| Group II | animal 5 | 61.5 |  | 63.1 |  |
|  | animal 6 | 68.9 |  | 65.6 |  |
|  | animal 7 | 58.2 |  | 57.9 |  |
|  | animal 8 | 76.3 |  | 79.3 |  |
| Group Average |  | 66.2 | 101 | 66.5 | 104 |
| Group III | animal 17 | 63.5 |  | 73.8 |  |
|  | animal 18 | 68.7 |  | 75.0 |  |
|  | animal 19 | 72.1 |  | 76.9 |  |
|  | animal 20 | 68.0 |  | 80.9 |  |
| Group Average |  | 68.9 |  | 76.5 | 120 |

What is claimed is:

1. A process of feeding sheep having a paunch containing a microflora of bacteria and protozoa which normally break down added synthetic aminoacids comprising feeding them fodder which goes to the paunch, said fodder containing an N-acyl-methionine of the formula

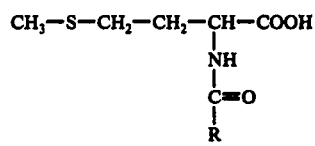

where R is an aliphatic hydrocarbon having 7 to 19 carbon atoms as a source of methionine which is not broken down in said paunch, the N-acyl-methionine being present in an amount effective to increase the growth of wool on sheep.

2. The process of claim 1 wherein the fodder is a base fodder and the N-acyl-methionine is present in an amount equivalent to 0.01 to 5% of methionine.

3. The process of claim 2 wherein the fodder includes grass.

4. The process of claim 2 wherein R is a straight chain hydrocarbon group.